United States Patent [19]

Parks et al.

[11] Patent Number: 5,250,040
[45] Date of Patent: Oct. 5, 1993

[54] FERRULE AND ENTERAL TUBE INCORPORATING A FERRULE

[75] Inventors: Stephen K. Parks, Redwood City; Udi Fishman, San Jose; Christine Decaria, Los Altos; Harry Park, San Jose, all of Calif.

[73] Assignee: Medical Innovations Corporation, Milpitas, Calif.

[21] Appl. No.: 10,908

[22] Filed: Jan. 28, 1993

Related U.S. Application Data

[60] Division of Ser. No. 632,776, Dec. 21, 1990, which is a continuation-in-part of Ser. No. 453,308, Dec. 21, 1989, abandoned.

[51] Int. Cl.$^5$ .................. A61M 25/00; A61M 5/32; F16L 25/00; B65D 55/00
[52] U.S. Cl. .................. 604/283; 604/282; 604/174; 285/177; 16/2
[58] Field of Search ............... 285/177; 604/280, 283, 604/905, 174, 175, 43–45, 264, 257, 282; 16/2, 108

[56] References Cited

U.S. PATENT DOCUMENTS

| | | | |
|---|---|---|---|
| 1,242,174 | 10/1917 | Gouch | 604/258 |
| 1,865,926 | 7/1932 | Laing | 16/108 X |
| 2,957,196 | 10/1960 | Kreider et al. | 16/2 |
| 2,961,691 | 11/1960 | Roy et al. | 16/2 |
| 3,817,561 | 6/1974 | Kay | 285/177 |
| 4,232,421 | 11/1980 | Tucker | 16/2 |
| 4,257,416 | 3/1981 | Prager | 604/80 X |
| 4,349,024 | 9/1982 | Ralston, Jr. | 604/905 X |
| 4,685,901 | 8/1987 | Parks | 604/96 |
| 4,701,162 | 10/1987 | Rosenberg | 604/103 |
| 4,774,940 | 10/1988 | Linder | 128/204.18 |
| 4,963,132 | 10/1990 | Gibson | 604/256 |
| 4,969,879 | 11/1990 | Lichte | 604/283 |
| 4,994,048 | 2/1991 | Metzger | 604/283 |
| 5,049,139 | 9/1991 | Gilchrist | 604/265 |
| 5,057,093 | 10/1991 | Clegg et al. | 604/283 |
| 5,171,216 | 12/1992 | Dasse et al. | 604/43 |

FOREIGN PATENT DOCUMENTS

| | | | |
|---|---|---|---|
| 2845346 | 4/1980 | Fed. Rep. of Germany | 604/283 |
| 1125735 | 11/1956 | France | 604/283 |
| 1380991 | 1/1975 | United Kingdom | 604/103 |

Primary Examiner—John D. Yasko
Assistant Examiner—Adam J. Cermak
Attorney, Agent, or Firm—Wilson, Sonsini, Goodrich & Rosati

[57] ABSTRACT

A ferrule for use as a medical device which maker mechanical connection with external connector tubes provided; the ferrule comprises an inner wall defining a conduit extending between an inlet opening and an outlet opening; a first taper lock surface is defined by a first region of the inner wall for forming a taper lock with a first connector portion having first dimensions; and a second taper lock surface is defined by a second region of the inner wall for forming a taper lock with a second connector portion having second dimensions.

14 Claims, 13 Drawing Sheets

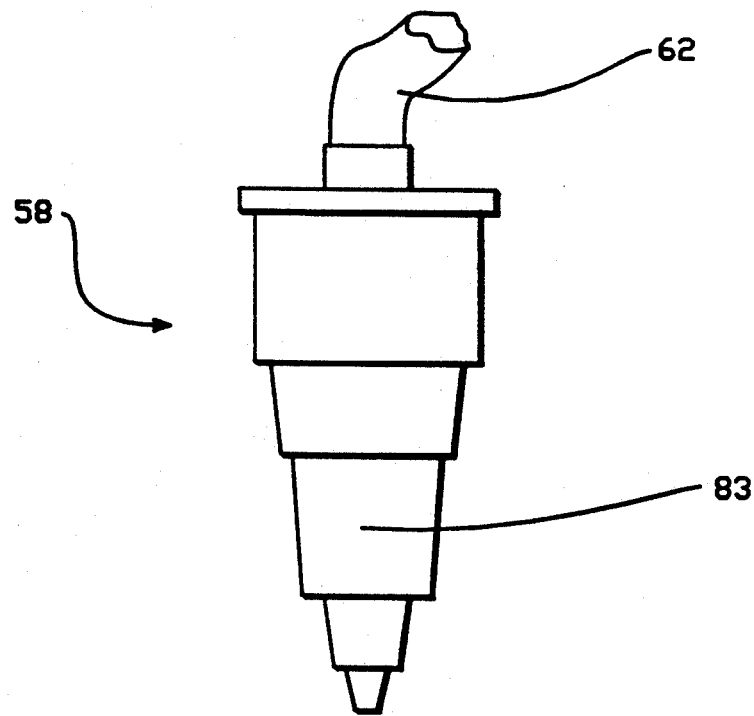
FIG.−3
(PRIOR ART)
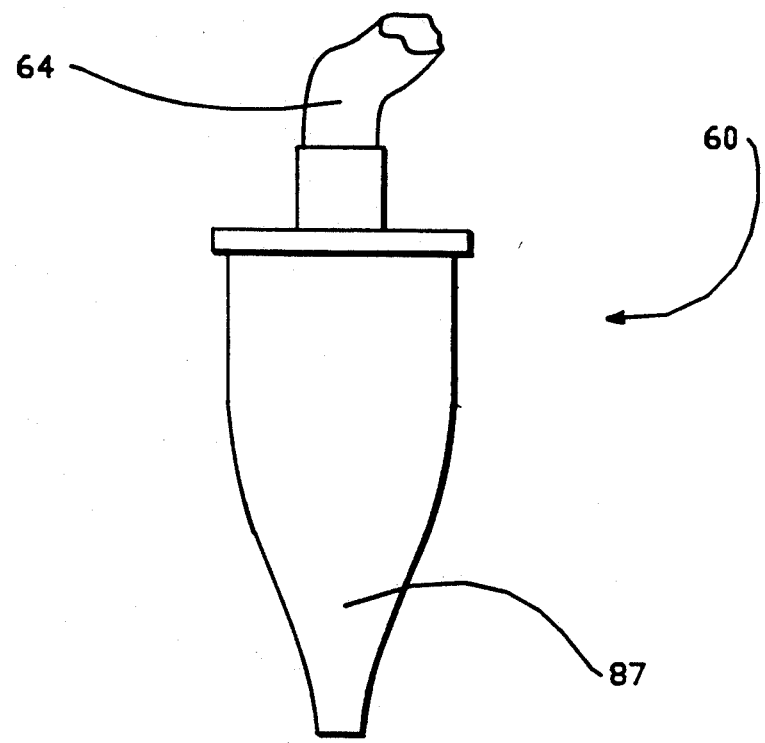
FIG.−4
(PRIOR ART)

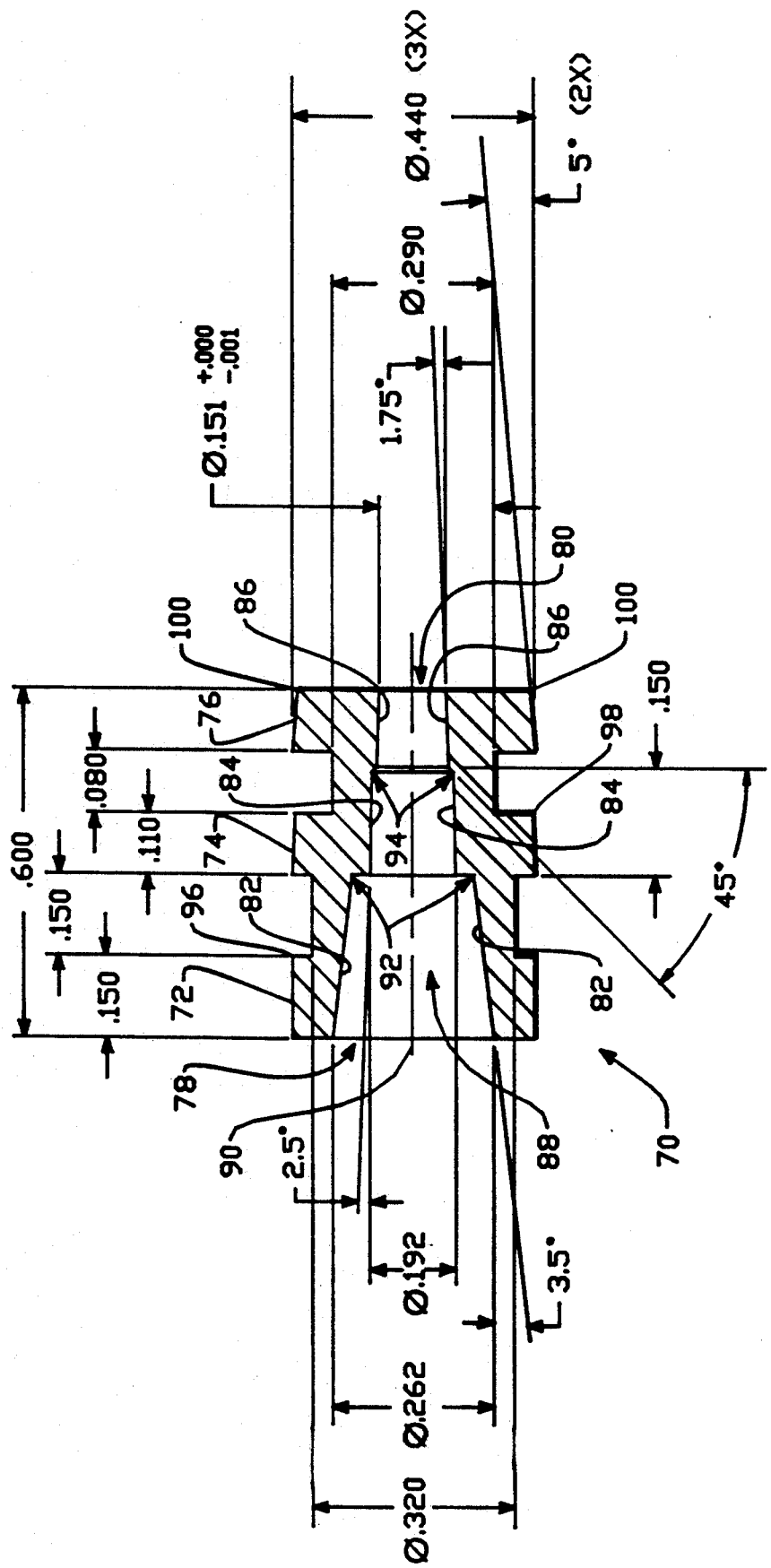
FIG.—7

FIG.—13

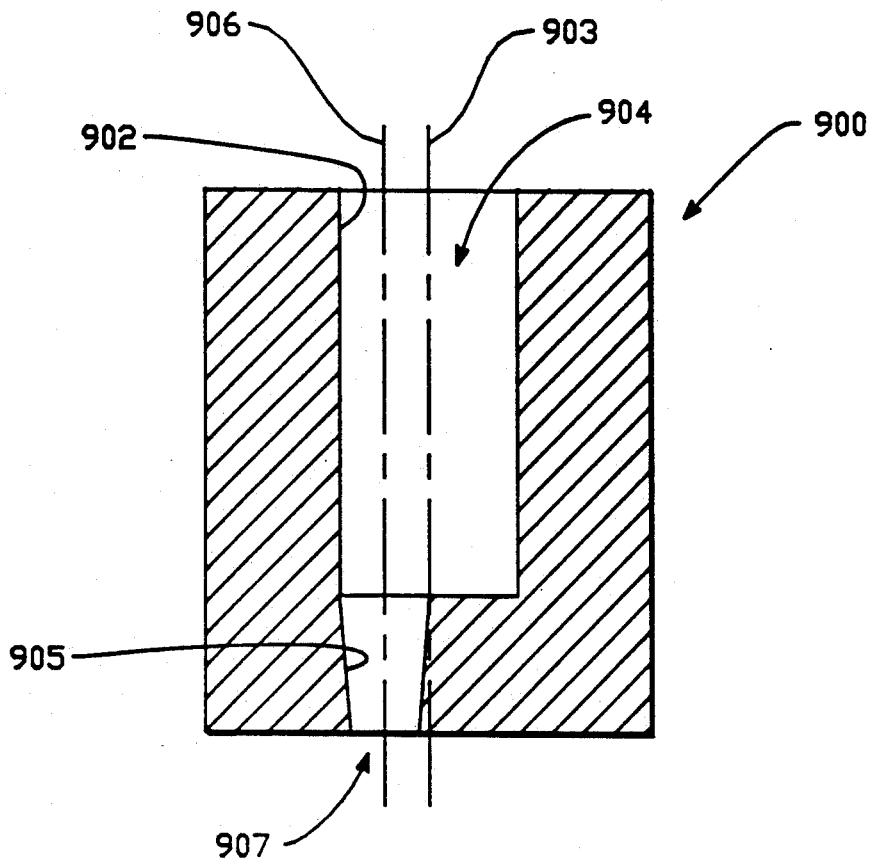
FIG.—20A
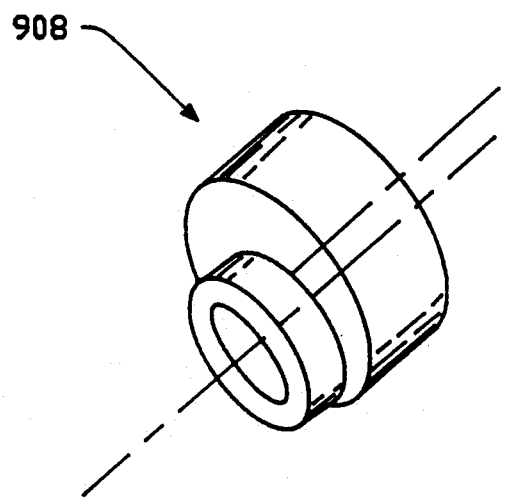
FIG.—20B

FERRULE AND ENTERAL TUBE INCORPORATING A FERRULE

This application is a divisional of application Ser. No. 07/632,776, filed Dec. 21, 1990, is a Continuation-in-part of Ser. No. 453,308 filed Dec. 21, 1989, entitled FERRULE AND ENTERAL TUBE INCORPORATION A FERRULE, now abandoned.

BACKGROUND OF THE INVENTION

1. Field of the Invention

The invention relates generally to enteral tubes and more particularly to mechanical connections between enteral tubes and feeding sets containing food or medication.

2. Description of the Related Art

Enteral tubes for providing food and medication to a patient are well known. For example, U.S. Pat. No. 4,666,433, entitled Gastrostomy Feeding Device, invented by Parks and issued May 19, 1987; and U.S. Pat. No. 4,701,163, entitled Gastrostomy Feeding Device, invented by Parks and issued Oct. 20, 1987; and U.S. Pat. No. 4,798,592, entitled Gastrostomy Feeding Device, invented by Parks and issued Jan. 17, 1989; and U.S. Pat. No. 4,685,901, entitled Gastro-Jejunal Feeding Device, invented by Parks and issued Aug. 11, 1987 disclose earlier feeding tubes.

Referring to the illustrative drawing of FIG. 1A, there is shown a perspective view of an earlier enteral feeding device 20. The device 20 includes an elongated tubular member 51 formed from a stretchable elastomeric material such as silicone. FIG. 1B is an illustrative cross-sectional view of the tubular member 51 of the earlier device. The member 51 defines a jejunal tube 22, a gastronomy tube 34 and a fluid line 46.

The jejunal feeding tube 22 includes an outlet end portion 24 which can extend through a patient's stomach into the jejunum. The jejunal tube outlet end portion includes perforations 26 which permit liquid food or medication to pass therethrough. The tube 22 is integrally connected to a jejunal tube inlet end portion 28 which defines a jejunal inlet port 30 having a removable plug cover 32.

The gastrostomy tube 34 is shorter than the jejunal tube 22 and includes a plurality of drainage inlets or food outlet ports such as inlet/outlet 36. A gastrostomy tube end portion 37 defines a gastrostomy inlet port 38 having a plug cover 40.

An inflatable balloon 42 is provided near the end of the gastrostomy tube 34 and is inflatable through a valve 44. The valve 44 is used to supply fluid to the balloon 42 through the fluid line 46.

Frictional contact between the elongated tubular member 51 and a locking ring 56 is sufficiently great to prevent the member 51 from moving further into the stomach. The locking ring 56 to remains in contact with a patient's abdominal wall during use. However, the frictional contact also is sufficiently low to permit adjustment of placement of the member 51 relative to a patient's abdomen.

Referring to the illustrative drawings of FIG. 2, there is shown a perspective view of an earlier device 20 in use. The inflated balloon 42 forms a gasket that seals the entrance to the stomach, and together with the locking ring 56, secures the device 20 in place.

While prior feeding tubes generally have been acceptable, there have been shortcomings with their use. In particular, for example, in order to provide food or medication to the jejunal inlet port 30 of device 20, a connector, such as a first connector 58 illustrated in FIG. 3 or a second connector 60 illustrated in FIG. 4, is inserted through the jejunal inlet port 30. The inserted connector 58 or 60 is mechanically coupled to the jejunal inlet port 30 and serves as a conduit between the jejunal tube 22 and an external feeding tube 62 or 64, shown in FIGS. 3 and 4. The external tube 62 or 64 is connected to a source of food such as a feeding bag (not shown).

In practice, connectors 58 or 60 such as those shown in FIGS. 3 and 4, for example, may be inserted into and removed from the jejunal inlet port 30 or the gastrostomy inlet port 38 numerous times during the course of use of the device 20 which can be installed in a patient's stomach for extended periods of time. As mentioned above, the member 51 which defines the jejunal tube inlet end 28, and the gastrostomy tube end portion 37 can be formed from a stretchable elastomeric material such as silicone. In order to produce an adequate mechanical coupling between the connector 58 or 60 and either the jejunal inlet port 30 or the gastrostomy inlet port 38, the connector is forced into place so as to produce a frictional engagement. Repeated insertions and removals of such connectors 58 or 60 can cause the jejunal inlet port 30 or the gastrostomy inlet port 38 to become somewhat stretched and deformed over time.

Unfortunately, as the jejunal and gastrostomy inlet ports 30, 38 become more and more stretched in this manner, the tendency of a medical attendant responsible for coupling such a connector to the inlet ports 30,38 often is to more forcibly push the connector into the jejunal or gastrostomy ports 30 or 38 resulting in still further stretching. Moreover, more force often must be exerted to dislodge a connector after such a forced insertion. Additionally, as the interior of the inlet ports 30, 38 becomes soiled with food oils, for example, an attendant may attempt to push a connector into the port even more forcibly in order to compensate for the slipperiness of such oils, causing further deformation of the port opening.

The problem of achieving a tight fit between a jejunal or gastrostomy inlet port 30 or 38 and such connectors 58 or 60, for example, has been exacerbated by the fact that in the past, such connectors often have been available in a variety of shapes and sizes. This variety will be apparent from the illustrative drawings of FIGS. 3 and 4 in which the first and second connectors 58, 60 have quite different shapes. Consequently, in the past it often has been desirable to construct jejunal or gastrostomy inlet ports, that can accommodate any of a variety of such differently shaped connectors. Unfortunately, such earlier inlet ports often could not readily accommodate such a variety of differently shaped connectors without the need to forcibly insert or forcibly remove the connectors.

Thus, there has been a need for a device to permit any of a variety of different shapes and sizes of connectors to be inserted into or removed from an inlet port of a feeding tube without the need to use excessive force and substantially without deforming the feeding tube inlet port. The present invention meets these needs.

SUMMARY OF THE INVENTION

In one aspect, the invention provides a ferrule for use with a feeding tube formed from a flexible material. The ferrule includes an inner wall defining a conduit extending between an inlet opening and an outlet opening. A first taper-lock surface is defined by a first region of the inner wall, and a second taper-lock surface is defined by a second region of the inner wall.

In another aspect, the invention provides a feeding device. The feeding device includes an elongated tube formed from a flexible material. An inlet end portion formed from the flexible material is integrally connected to the elongated tube. The inlet end portion defines an inlet port opening. A ferrule is disposed within the inlet end portion. The ferrule includes an inner wall defining a conduit extending between an inlet opening and an outlet opening. A first taper-lock surface is defined by a first region of the inner wall, and a second taper-lock surface is defined by a second region of the inner wall.

Thus, the present invention provides a ferrule and feeding device that can readily form a taper lock with connectors without the use of excessive force. Conversely, connectors can be readily removed from such a ferrule or feeding device without the use of excessive force. Consequently, a feeding tube is not as likely to be stretched out of shape through repeated insertions and removals of such connectors.

These and other features and advantages of the present invention will become more apparent from the following description of exemplary embodiments thereof, as illustrated in the accompanying drawings.

BRIEF DESCRIPTION OF THE DRAWINGS

The purpose and advantages of the present invention will be apparent to those skilled in the art from the following detailed description in conjunction with the appended drawings in which:

FIGS. 3 and 4 are side elevation views of earlier connectors for insertion into end portions of a feeding tube;

FIG. 7 is a cross-sectional side elevation view of the ferrule of FIG. 5;

FIG. 20A is a cross-sectional side elevation view of an alternative embodiment of a ferrule in accordance with the invention in which first and second tapered inner wall regions are offset from each other; and FIG. 20B is a perspective view of a connector to lock in the ferrule of FIG. 20A.

DETAILED DESCRIPTION OF THE PREFERRED EMBODIMENT

The present invention comprises a novel ferrule and a related enteral feeding device incorporating a ferrule. The following description is presented to enable any person skilled in the art to make and use the invention, and is provided in the context of particular applications and their requirements. Various modifications t the preferred embodiments will be readily apparent to those skilled in the art, and the generic principles defined herein may be applied to other embodiments and applications without departing from the spirit and scope of the invention. Thus, the present invention is not intended to be limited to the embodiments shown, but is to be accorded the widest scope consistent with the principles and features disclosed herein.

Figure 1A:
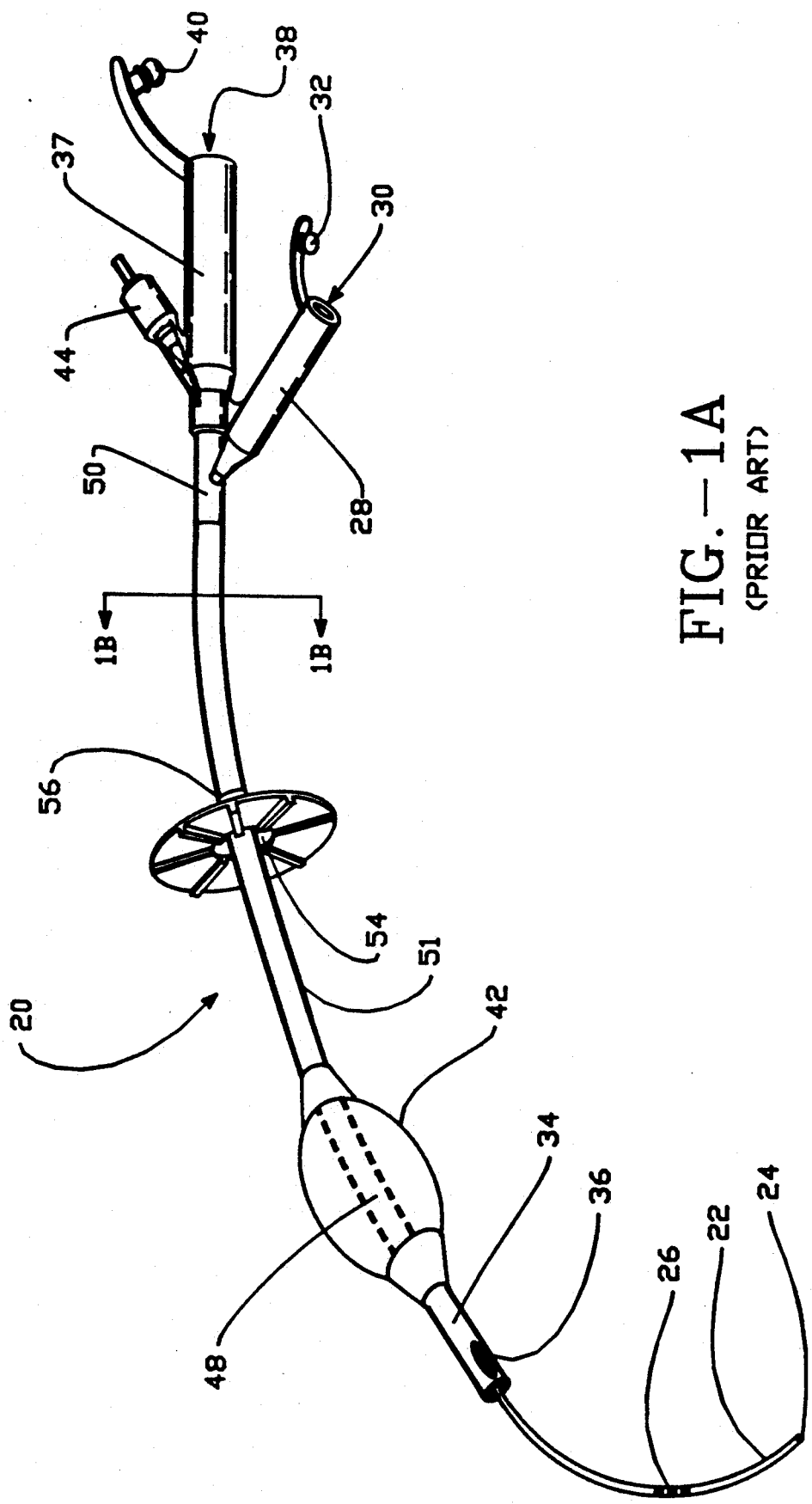
FIG. 1A is a perspective view of an earlier feeding tube.
Figure 1B:
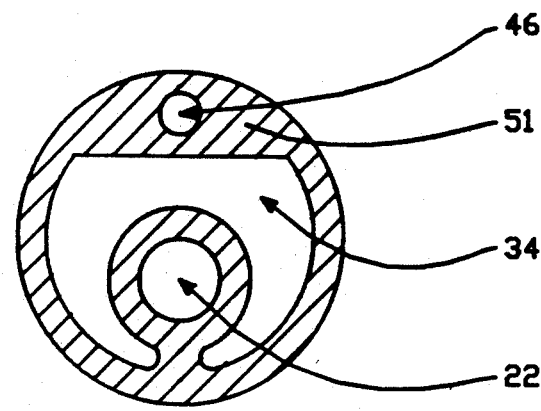
FIG. 1B is a cross-sectional view along line 1—1 of FIG. 1A illustrating the disposition of the jejunal and qastrostomy tubes and the connecting line.
Figure 2:
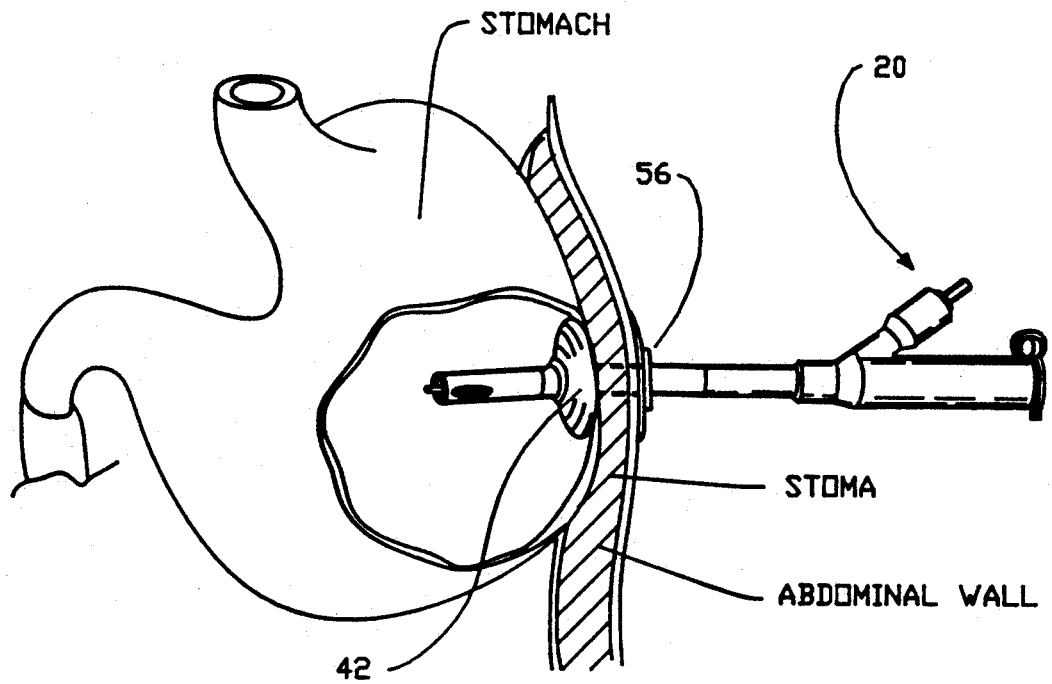
FIG. 2 is a perspective partially cutaway view of an earlier feeding tube installed in a patient.
Figure 5:
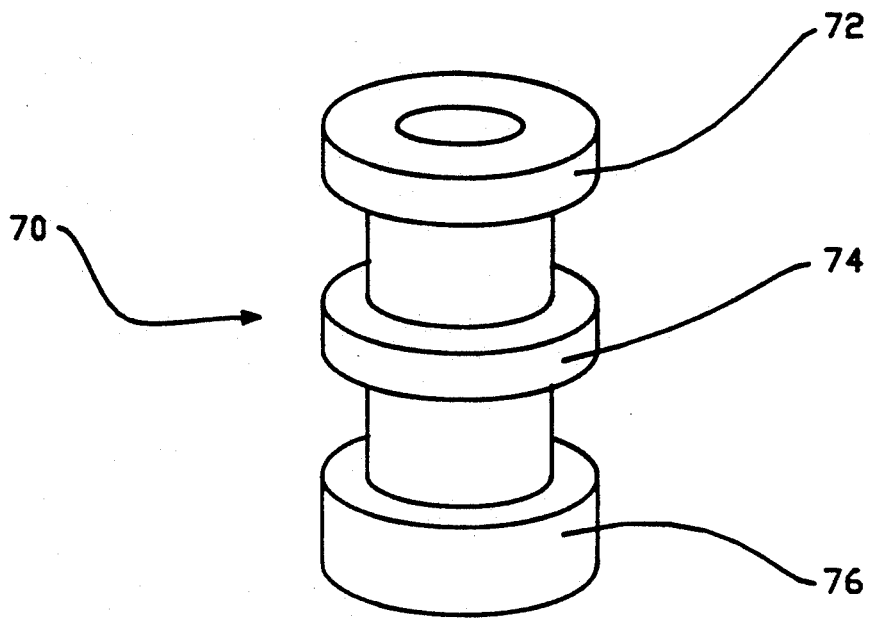
FIG. 5 is a perspective view of a ferrule in accordance with the present invention.
Figure 6A:
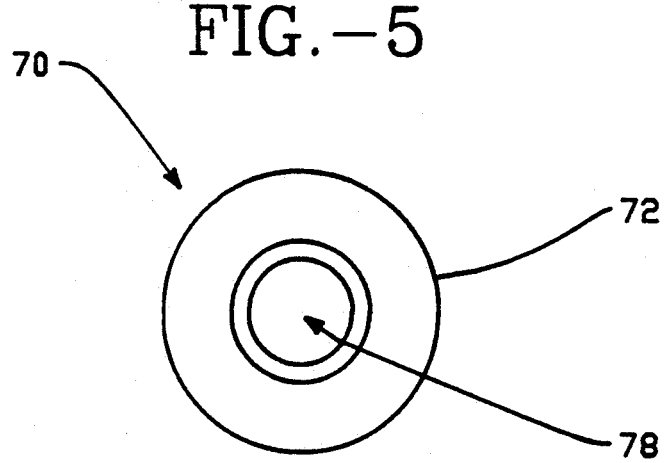
FIGS. 6A and 6B are top and bottom elevation views of the ferrule of FIG. 5.
Figure 6B:
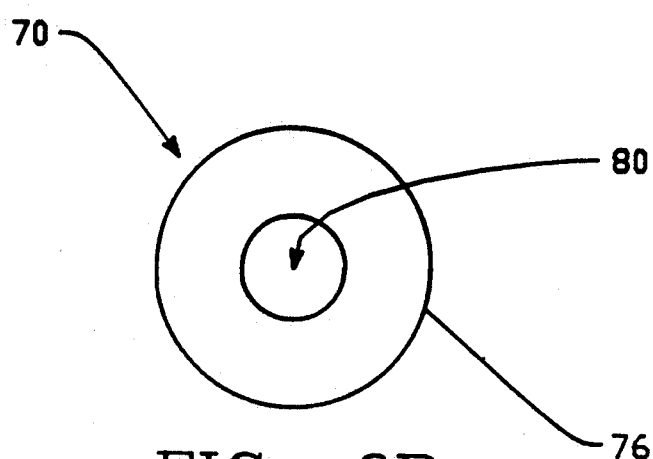

Referring to the illustrative drawings of FIG. 5, there is shown a perspective view of a ferrule 70 in accordance with a present embodiment of the invention. The ferrule 70 is generally cylindrical in shape and has top, middle and bottom annular ribs 72, 74 and 76 extending outwardly therefrom. FIGS. 6A and 6B respectively show top elevation and bottom elevation views of the ferrule 70. In FIG. 6A, there is shown an inlet opening 78 surrounded by the top annular rib 72. In FIG. 6B, there is shown an outlet opening 80 surrounded by the bottom annular rib 76. In the preferred embodiment, the ferrule 70 is formed from a hard substantially non-deformable material such as plastic, metal, glass or polyvinylchloride. Preferably the ferrule 70 is formed from a material that is acid-resistant and gamma-stabilized so that it can withstand a sterilization process involving irradiation.

The illustrative drawing of FIG. 7, shows a cross-sectional side elevation view of the ferrule 70. First, second and third interior wall regions 82, 84 and 86 define a conduit 88 extending between the inlet opening 78 and the outlet opening 80. The respective first, second and third interior wall regions 82, 84 and 86 each have substantially cylindrical contours and are aligned along a central axis 90 of the conduit 88.

As explained more fully below, the first, second and third interior wall regions define three separate taper lock surfaces. Each of these three interior wall regions can be sized and contoured to conform to the shape of a different connector portion from a different connector. Neither a connector nor any portion of a connector forms any part of the present invention. For example, the first interior wall region 82 can be sized and contoured to conform to the shape of a portion 83 of the first connector 58 of FIG. 3. The second interior wall region 86, for example, can be sized and contoured to conform to the shape of a portion 87 of the second connector 60 of FIG. 4. It will be appreciated that the interior wall regions of FIG. 7 are drawn to a different scale than the connectors of FIGS. 3 and 4. Moreover, the second interior wall region 84, for example, can be sized and contoured to conform to the shape of yet another connector (not shown).

A taper lock is caused by a frictional engagement force that results when a connector becomes lodged within the ferrule 70. The different sizing and contouring of the three different interior wall regions 82, 84 and 86 ensures that differently sized and contoured connector portions can become lodged against different interior wall regions.

Thus, when the first connector 58 is inserted into the inlet opening 78 of the ferrule 70, it becomes lodged against the first interior wall region, forming a taper lock with it. Likewise, when the second connector 60 is inserted into the inlet opening 78 of the ferrule 70, it becomes lodged against the third interior wall region 86, forming a taper lock with it.

A more detailed description of the sizing and contour of the ferrule 70 follows. The first interior wall region 82 has interior walls that are inclined relative to the central axis 90 so as to define a generally conical shape in which a diameter of a first segment of the conduit 88 defined by the first interior wall region 82 decreases with increasing distance from the inlet opening 78. A first interior annular shoulder 92 demarcates the end of the first interior wall region 82.

A second segment of the conduit 88 is defined by the second interior wall region 84 which also is substantially conical in shape. Like the first interior wall region, the interior walls of the second interior wall region 84 are inclined relative to the central axis 90 such that the diameter of a second conduit segment decreases with increasing distance from the inlet opening 78. A second interior annular shoulder 94 demarcates the end of the second interior wall region 84.

A third segment of the conduit 88 is defined by the third conical interior wall region 86. The interior walls of the third interior wall region are inclined relative to the central axis 90 such that the diameter of the third conduit segment decreases with increasing distance from the inlet opening 78. In the presently preferred embodiment, the dimensions of the third interior wall region are those of a luer. Moreover, it will be appreciated that in operation, a taper lock between a connector portion such as portions 83 or 87 inserted into the inlet opening 78 results because the diameter of an interior wall region, such as region 82, 84 or 86, decreases or tapers down, with increasing distance from an inlet to the region. It is the tapered inner wall region diameter of regions 82, 84 or 86 that facilitate the formation of taper locks in these wall regions. Moreover, it is desirable that the taper lock form a liquid tight seal.

One will appreciate that, although the presently preferred embodiment discloses smooth inner wall regions 82, 84 and 86, a taper lock can be formed in which inner wall regions have contours formed in them such as ridges, steps or bumps. In alternative embodiments such as those discussed below in relation to FIGS. 14, 16, 17 and 19, for example, spiral threaded ridges or steps or other structures formed in inner wall regions can afford a better lock by permitting the twisting of a connector portion into engagement with the inner wall regions.

Figure 14:
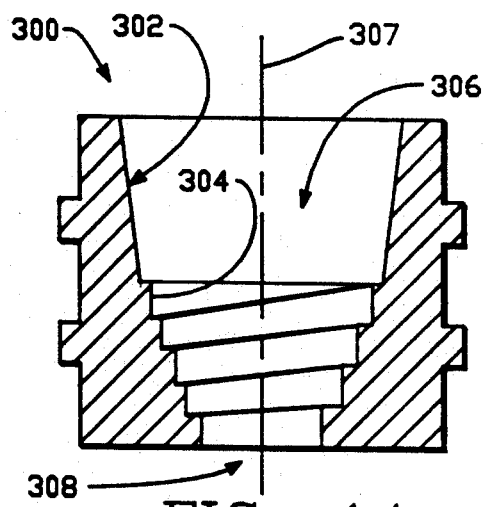
FIG. 14 is a cross sectional side elevation view of an alternative embodiment of a ferrule in accordance with the invention in which a locking taper inner wall region forms a concentric spiral step of decreasing diameter between an inlet opening and an outlet opening.

In an alternative embodiment of a ferrule 300 illustrated in the drawings of FIG. 14, tapered inner walls 302 form a smooth taper about a central axis 307 within a first inner wall segment such that the inner wall diameter decreases with increasing distance from an inlet opening 306. In a second inner wall segment, inwardly extending concentric ridges 304 form a spiral step about the central axis 307, such that the inner wall diameter decreases with increasing distance from the inlet opening 306. The tapered inner walls 302 and the spiral ridges 304 are concentrically aligned with the central axis 307 which extends between the inlet opening 306 and an outlet opening 308. One will appreciate that a taper lock can be formed with the surfaces of the first or second inner wall regions.

Figure 15:
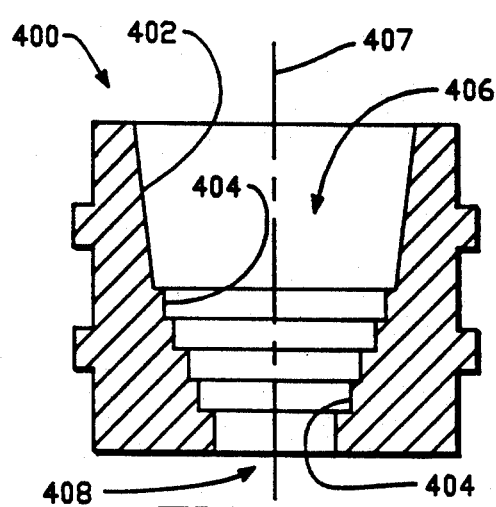
FIG. 15 is a cross-sectional side elevation view of an alternative embodiment of a ferrule in accordance with the invention in which a locking taper inner wall region forms a series of concentric steps of decreasing diameter between an inlet opening and an outlet opening.

In an alternative embodiment of a ferrule 400 illustrated in the drawings of FIG. 15, tapered inner walls 402 form a smooth taper about a central axis 407 within a first inner wall segment such that the inner wall diameter decreases with increasing distance from an inlet opening 406. In a second inner wall segment, inwardly extending concentric ridges 404 form a series of concentric steps about the central axis 407, such that the inner wall diameter decreases with increasing distance from the inlet opening 406. The tapered inner walls 402 and the ridges 404 are concentrically aligned with a central axis 407 which extends between the inlet opening 406 and an outlet opening 408. A taper lock can be formed either with surfaces of the first or second inner wall segments.

Figure 16:
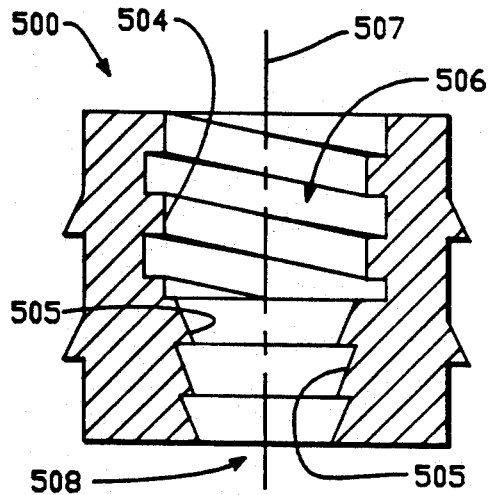
FIG. 16 is a cross-sectional side elevation view of an alternative embodiment of a ferrule in accordance with the invention in which an inner wall region forms a concentric spiral path within a first segment between an inlet opening and an outlet opening and forms a series of concentric steps within a second segment between the inlet opening and the outlet opening.

In an alternative embodiment of a ferrule 500 illustrated in the drawings of FIG. 16, a first inner wall segment includes a spiral-threaded path 504 about a central axis 507. A connector (not shown) having appropriately sized outwardly extending spiral threads can be screwed into place within the first inner wall segment. In a second inner wall segment, inwardly extending concentric inclined steps 505 are formed about the central axis 507. For each respective step 505, the inner wall diameter decreases with each increasing distance from an inlet opening 506. The spiral ridges 504 and the steps 505 are concentrically aligned with the central axis 507 which extends between the inlet opening 506 and an outlet opening 508.

Figure 17:
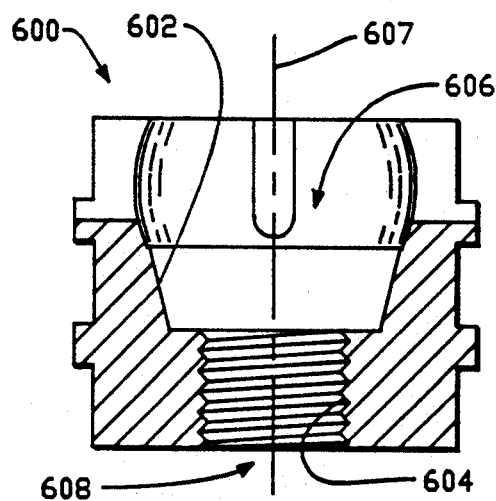
FIG. 17 is a cross-sectional side elevation view of an alternative embodiment of a ferrule in accordance with the invention in which an inner wall region forms a ball socket within a first segment, forms a taper lock surface in which a tapered inner wall diameter gradually decreases with increasing distance from an inlet opening within a second segment and forms an inner thread within a third segment between an inlet opening and an outlet opening.

In an alternative embodiment of a ferrule 600 illustrated in the drawings of FIG. 17, in a first inner wall segment, inner walls 603 are shaped to conform to a ball connector (not shown). In a second segment, tapered inner walls 602 form a smooth taper about a central axis 607 such that the inner wall diameter decreases with increasing distance from an inlet opening 606. In a third segment, inwardly extending concentric spiral ridges 604 form a spiral thread sized to form a threaded interconnect with an appropriately sized connector (not shown) having complementary spiral threads. The first inner walls 603 inner walls 602 and the concentric ridges 604 are concentrically aligned with the central axis 607 which extends between the inlet opening 606 and an outlet opening 608.

Figure 18:
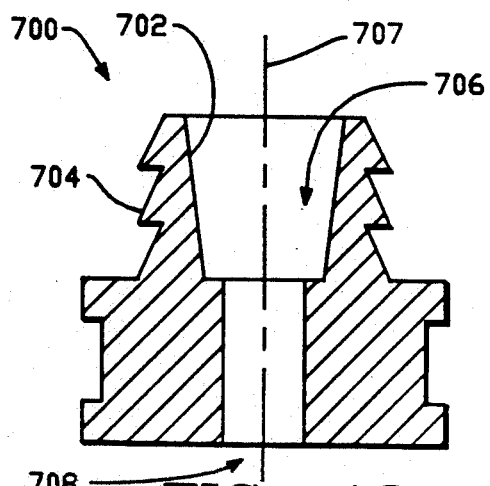
FIG. 18 is a cross-sectional side elevation view of an alternative embodiment of a ferrule in accordance with the invention in which a tapered inner wall diameter gradually decreases with increasing distance from an inlet opening within a first segment and in which an exterior wall forms a external barbed connector surrounding the tapered inner wall segment.

In an alternative embodiment of a ferrule 700 illustrated in the drawings of FIG. 18, tapered inner walls 702 form a smooth taper about a central axis 707 within a first segment of the ferrule 700 such that the inner wall diameter decreases with increasing distance from an inlet opening 706. Outwardly extending barbs 704 are formed in an exterior wall of the first segment and are used to form a gripping interconnect with an appropriately sized connector (not shown). The tapered inner walls 702 are concentrically aligned with the central axis 707 which extends between the inlet opening 706 and an outlet opening 708.

Figure 19:
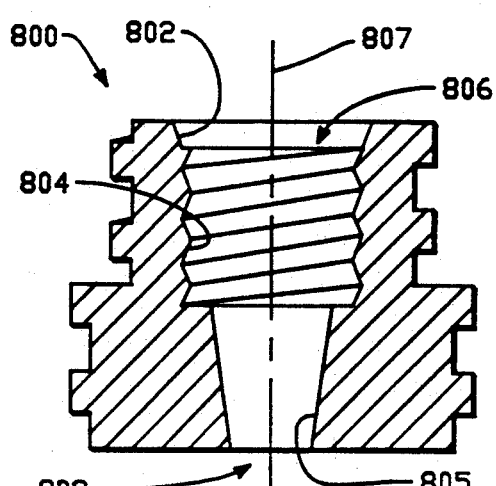
FIG. 19 is a cross-sectional side elevation view of an alternative embodiment of a ferrule in accordance with the invention in which a first tapered inner wall diameter gradually decreases with increasing distance from an inlet opening in a first segment, in which the inner wall forms an inner ridge which follows a threaded spiral path in a second segment, and in which a second tapered inner wall diameter gradually decreases with increasing distance from the inlet opening within a third segment.

In an alternative embodiment of a ferrule 800 illustrated in the drawings of FIG. 19, first tapered inner walls 802 form a smooth taper about a central axis 807 within a first inner wall segment such that the inner wall diameter decreases with increasing distance from an inlet opening 806. In a second inner wall segment, inwardly extending concentric spiral ridges 804 form a spiral thread about the central axis 807, such that an appropriately sized connector having complementary spiral threads (not shown) can be secured in place. Second tapered inner walls 805 form a second smooth taper about the central axis 807 within a third inner wall segment such that the inner wall diameter decreases with increasing distance from the inlet opening 806. The first and second tapered inner walls 802 and 805 and the spiral ridges 804 are concentrically aligned with the central axis 807 which extends between the inlet opening 806 and an outlet opening 808.

In FIG. 20A, an alternative embodiment of a ferrule 900 used to form an offset lock is shown. As illustrated in the drawings of FIG. 20A, inner walls 902 are formed about a first axis 903 within a first inner wall segment. In a second inner wall segment, second inner walls 905 are formed about a second axis 906. The first and second tapered inner walls 902, 905 define a path between inlet opening 904 and an outlet opening 907.

In FIG. 20B, there is shown a connector 908, which forms no part of the present invention, which can be interconnected with the offset lock ferrule 900 of FIG. 20A.

Thus, it will be appreciated that a ferrule in accordance with the present invention can be constructed with any of a variety of gripping mechanisms for gripping different external connectors (which form no part of the present invention). Moreover, while a variety of combinations of gripping mechanisms such as smooth tapers, spiral and non-spiral steps, threads, barbs, ball and socket and offset locks have been specifically described, alternative gripping mechanisms and different combinations of gripping mechanisms can be employed without departing from the invention.

It will be understood that an alternative ferrule (not shown) could be constructed in accordance with the invention in which different taper lock regions were aligned along different parallel nonaligned axes or along different nonparallel axes as explained below with respect to FIGS. 11 and 12.

The outer edges of the middle and bottom outwardly extending annular ribs 74, 76 are inclined relative to the central axis 90 such that the diameter of each of these respective annular ribs 74, 76 decreases with increasing distance from the inlet opening 78. Moreover, the respective shoulders 96, 98 and 100 of the top, middle and bottom annular rings are rounded. The inclined and rounded edges of the outwardly protruding annular ribs can facilitate the process of inserting the ferrule 70 into an inlet end portion of a feeding tube as explained more fully below.

Figure 8:
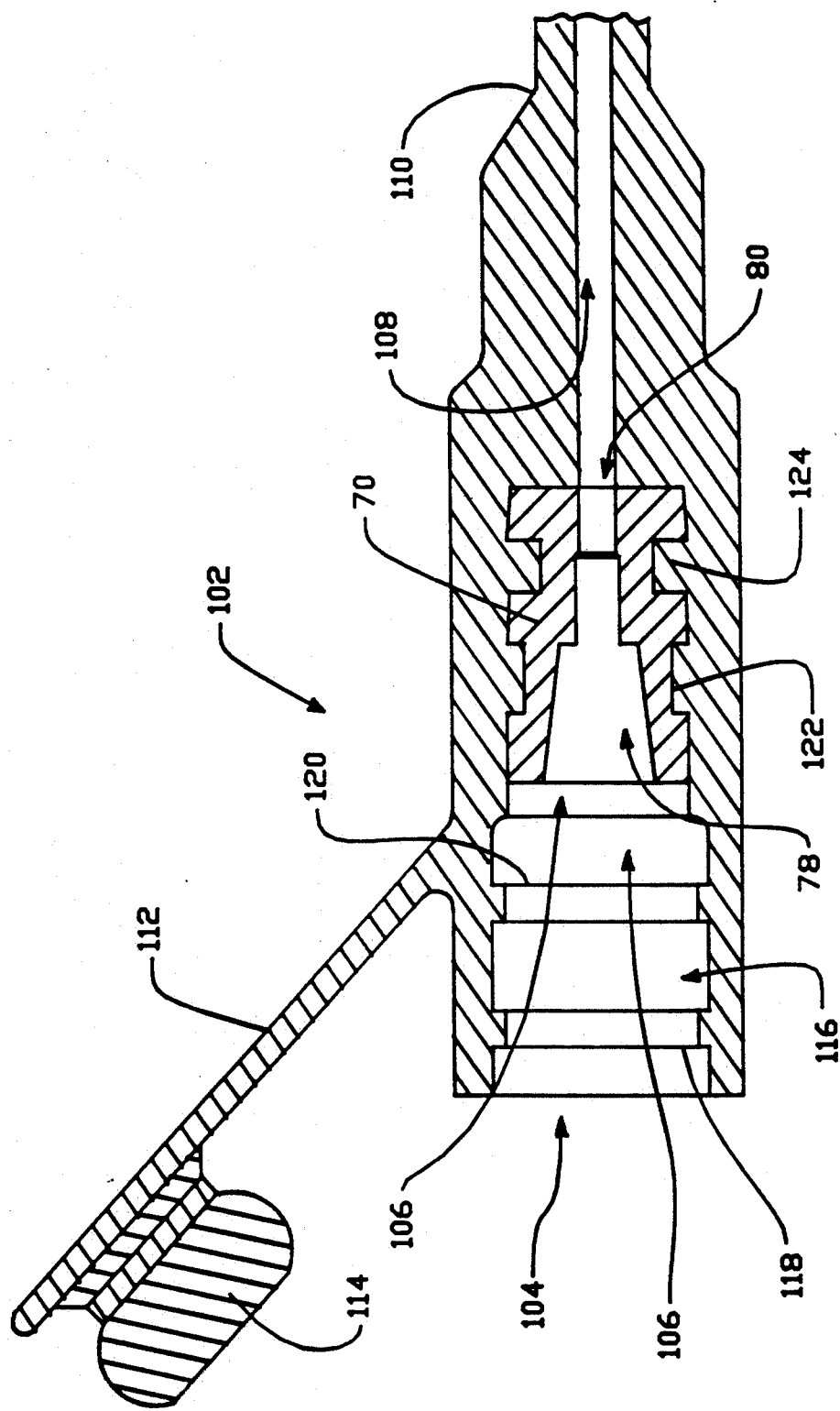
FIG. 8 is a cross-sectional side elevation view of the ferrule of FIG. 5 incorporated into an end portion of a feeding tube.

Referring now to FIG. 8, there is shown a cross-sectional elevation view of an inlet end portion 102 of an enteral tube, in accordance with the presently preferred embodiment of the invention, which incorporates the ferrule 70. An enteral feeding tube feeds into the digestive tract. The feeding tube is formed from an elastomeric silicone material and can be formed by injection molding. The inlet end portion 102 defines an inlet port opening 104 and defines a first passage 106 between the inlet port opening 104 and the inlet opening 78 of the ferrule 70. The outlet opening 80 of the ferrule 70 communicates with a second elongated passage 108 defined by an elongated tube portion 110 of the feeding tube, only a short segment of which is shown.

An arm 112 is integrally formed with the end portion 102 and has a plug 114 extending therefrom. The arm 112 can be bent, and the plug 114 can be inserted into the inlet port opening 104, whereupon it becomes lodged in a space 116 between two inwardly projecting annular protrusions 118, 120 integrally formed in the inlet end portion 102. In this manner, the opening 104 can be closed when the end portion 102 is not in use.

Moreover, when the inlet end portion 102 is in use and a connector, such as the first or the second connector 58 or 60, is inserted through the inlet port opening 104 and has formed a taper lock with one of projecting annular protrusions 118, 120 abut against the connector. The protrusions 118, 120 advantageously produce a fluid seal with a connector inserted through the inlet port opening 104 to prevent fluid leakage from the opening 104. It will be appreciated that such annular protrusions alternatively could be invalid within an annular inset (not shown) in the ferrule 70 or could be positioned downstream from the ferrule 70 adjacent to the ferrule outlet port 80.

The outwardly projecting annular ribs 74, 76, 78 of the ferrule 70 grip inwardly projecting annular ribs 122, 124 which are integrally formed in the end portion and which are contoured to fit snugly between the ribs 74, 76, 78. In this manner, the ribs 74, 76, 78 hold the ferrule 70 in place within the inlet end portion 102. It will be appreciated that although annular ribs 74, 76, 78 are used to grip the end portion 102, differently shaped objects could be used to accomplish that purpose. For example, the outer surface of the ferrule 70 could be abraded so as to roughen it to allow it to grip the interior of the end portion 102. Alternatively, for example, the outer surface of the ferrule 70 could have protrusions in the shape of individual upstanding barbs or in the shape of helical ridges. In certain applications, for example, it may be desirable to install a removable ferrule in the end portion 102. Annular ribs 74, 76 of ferrule 70 afford such removability as do similar annular ribs of ferrule 126 and of the alternative ferrules of FIGS. 14-19. Removability can be important, for example, in situations where one type of ferrule is to be removed and another type is to be inserted in order to accommodate a variety of different connectors. For example, in one application a connector (which forms no part of the present invention) may be suited to connection to a barbed gripping mechanism such as the barbs 704 of ferrule 700 of FIG. 18. Consequently, it will be desirable to install such a barbed ferrule. If necessary, a previously installed ferrule will have to be removed.

Figure 9:
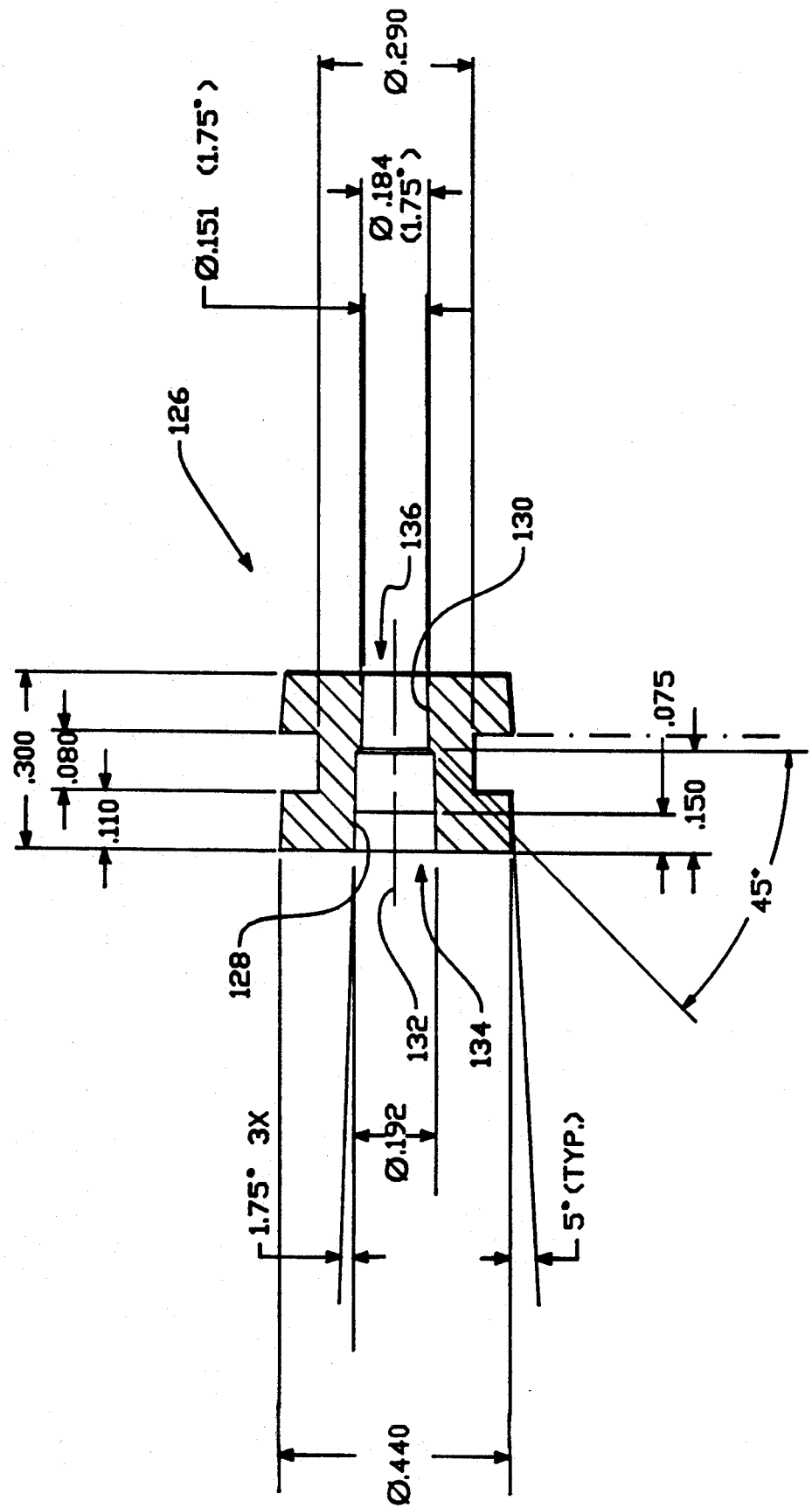
FIG. 9 is an alternative embodiment of a ferrule in accordance with the invention.

Referring to the illustrative drawings of FIG. 9, there is shown an alternative embodiment of a ferrule 126 in accordance with the invention. The alternative ferrule 126 is generally similar to the presently preferred ferrule 70 except that it includes only two interior wall regions 128, 130 for use as taper lock surfaces instead of the three such regions 82, 84, 86 of the ferrule 70. The ferrule 126 includes a conduit having a central axis 132. The conduit extends between an inlet opening 134 and an outlet opening 136. Thus, the structure and operation of the alternative ferrule 126 will be appreciated from the above description of the preferred ferrule 70 and need not be set forth herein.

Figure 10:
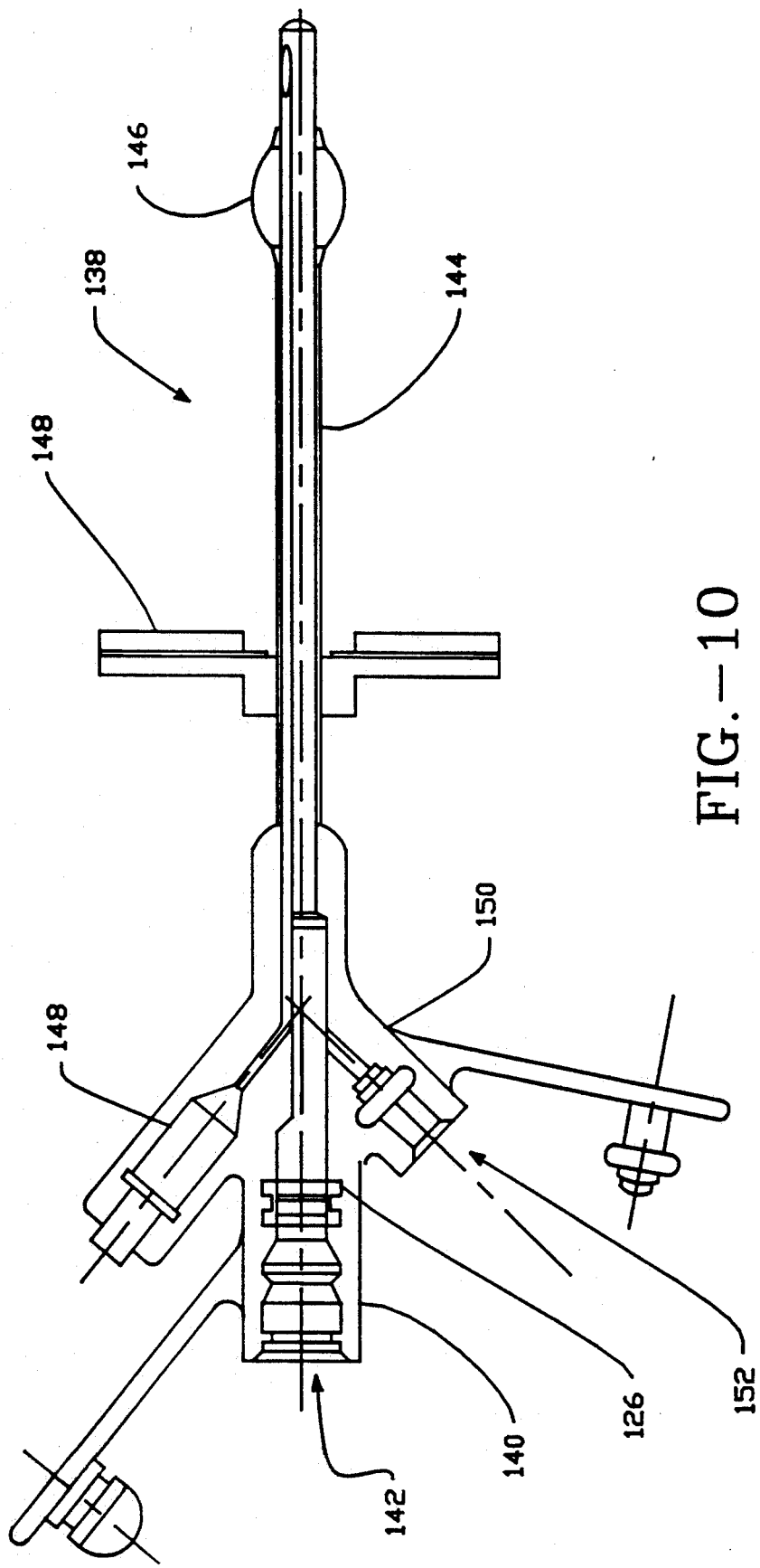
FIG. 10 is a cross-sectional side elevation view of the ferrule of FIG. 9 incorporated into a feeding tube.

FIG. 10 shows a cross-sectional elevation view of an enteral tube 138 which incorporates the alternative ferrule 126. The enteral tube 138 includes an inlet end portion 140 defining an inlet port opening 142. It also includes an elongated tube member 144, an inflatable balloon 146 and a locking ring 148. The enteral tube 138 also includes a valve 148 for use in providing fluid to the balloon 146 and another end portion 150 defining another port opening 152 that can be used to provide medication.

In order to manufacture a feeding tube that incorporates a ferrule like that of FIGS. 7 or 9, the ferrule can be mounted on a pin, for example, and a silicone end portion can be injection molded about it. Alternatively, the silicone end portion can be produced first, and later the ferrule can be mounted on a mandril and be forced into position within the end portion. In this alternative manufacturing approach, the inclined and rounded outer portions of the outwardly extending annular ribs are useful to ensure that the ferrule does not become snagged as it is forced into the end portion.

It will be appreciated that while the presently preferred embodiment of FIGS. 7 and 9 include interior wall regions 82, 84, 86 and 128,130 for use in forming taper locks with differently sized connector portions, alternative locking mechanisms can be employed without departing from the invention. For example, a thread connection, barbs, a ball joint or a quick spike joint could be employed. Moreover, the interior wall regions need not be smooth or gradually decreasing in diameter to be employed in forming a taper lock with a connector.

Figure 11:
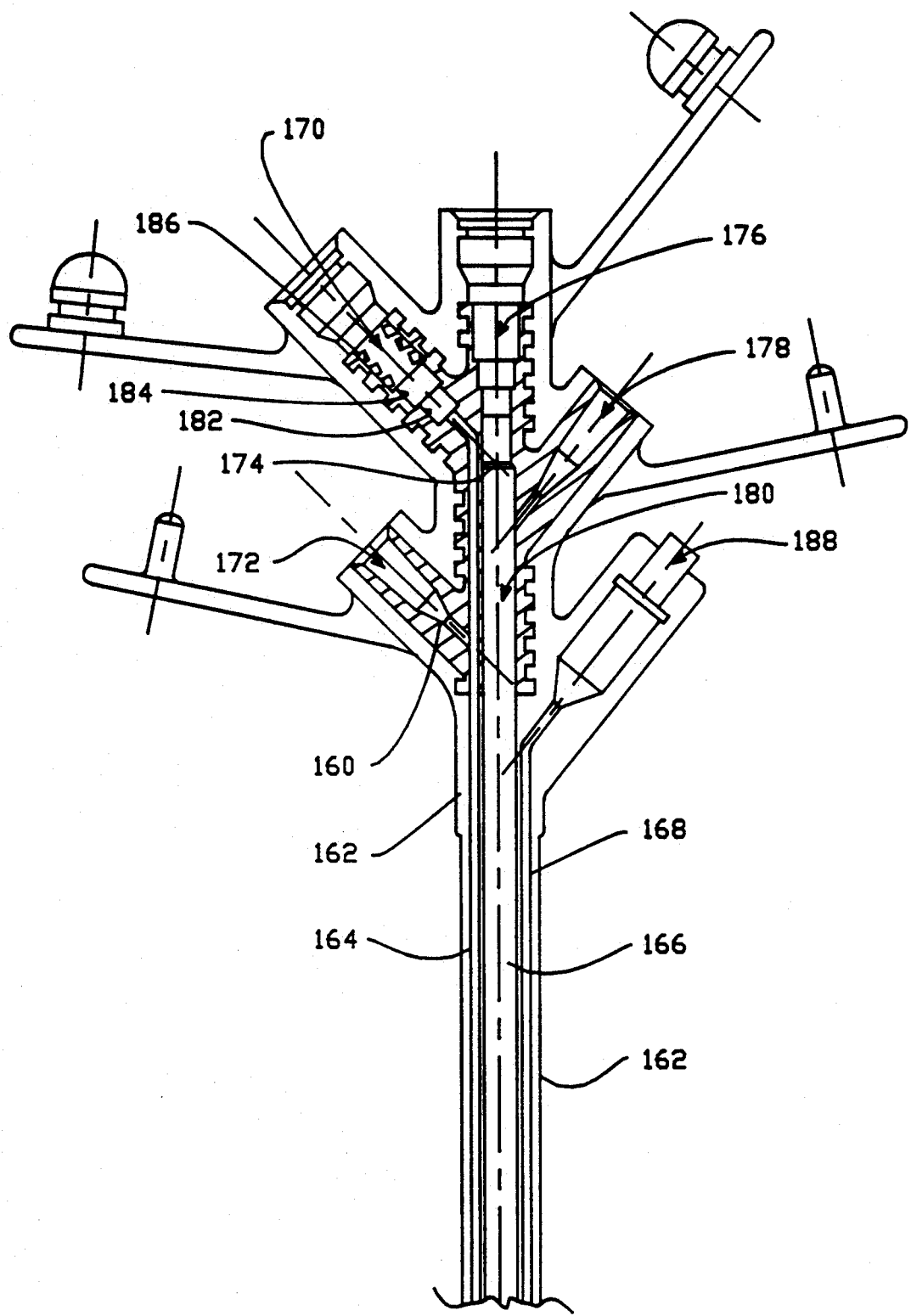
FIG. 11 is a cross-sectional side elevation view of a first branched ferrule in accordance with the invention.

Referring to the illustrative drawings of FIG. 11, there is shown a first branched ferrule in accordance with the invention. The first branched ferrule 160 is disposed within an elongated tube member 162 which defines a jejunal tube 164, a gastrostomy tube 166 and a fluid line 168. The elongated tube member 162 is formed from a flexible elastomeric material such as silicone. The first branched ferrule 160 defines first and second jejunal inlet openings 170, 172 that provide fluid access, through a first tubule 174, to the jejunal tube 164. First and second gastrostomy inlet openings 176, 178 provide fluid access, through a second tubule 180, to the gastrostomy tube 166. The first jejunal and gastrostomy inlet openings 170, 176, for example can be used to receive food, and the second jejunal and gastrostomy inlet openings 172, 178, for example, can be used to receive medicine. The elongated tube member 162 defines a fluid port 188 in which a valve (not shown) can be installed to control the flow of a fluid through the fluid line 168.

A region accessible through the first jejunal inlet opening 170 includes first and second conical inner wall regions 182,184 that can be used to form taper locks with a connector portion (not shown). That same region accessible through the first jejunal inlet opening 170 also defines threads 186 that can be threaded to a complementary threaded connector (not shown). Thus, the first branched ferrule 160 can form a taper lock or a threaded engagement with different connectors inserted into the first jejunal inlet opening 170.

Figure 12:
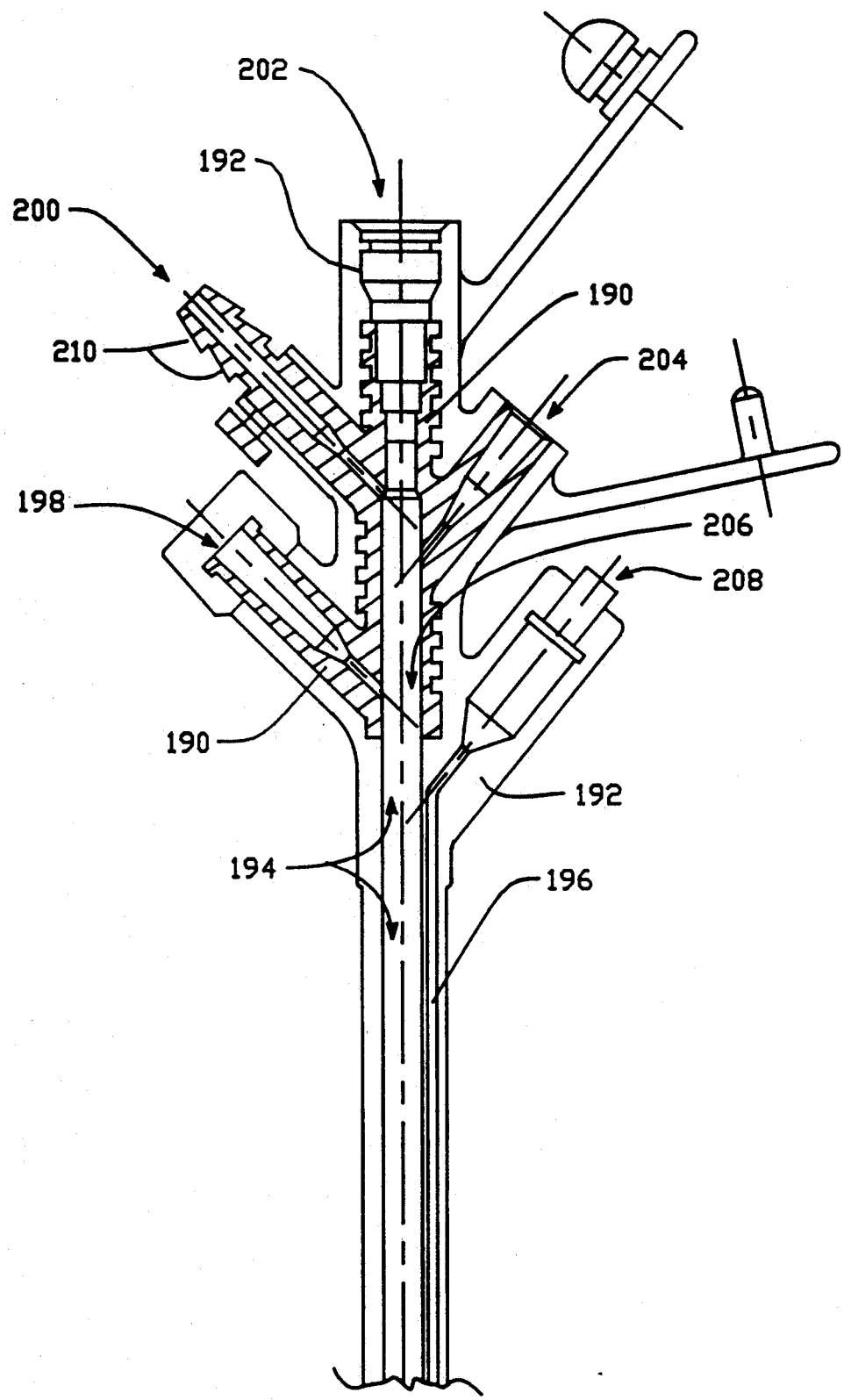
FIG. 12 is a cross-sectional side elevation view of a second branched ferrule in accordance with the invention.

Referring to the illustrative drawings of FIG. 12, there is shown =second branched ferrule 190 in accordance with the invention. The second branched ferrule 190 is disposed within an elongated tube member 192 which defines a single enteral tube 194 and a fluid line 196. The second branched ferrule 190 defines first, second, third and fourth inlet openings 198, 200, 202, 204, each of which provides fluid access to a single tubule 206 that communicates with the single enteral tube 194. The elongated tube member 192 defines a fluid port 208 in which a valve (not shown) can be installed to control the flow of fluid through the fluid line 196

Two conical barbs 210 upstand from the second branched ferrule 190 about the second inlet port external to the elongated tube member 192. The barbs 210 can be used to engage and hold in place a connector (not shown) formed from a flexible material such as silicone.

Figure 13:
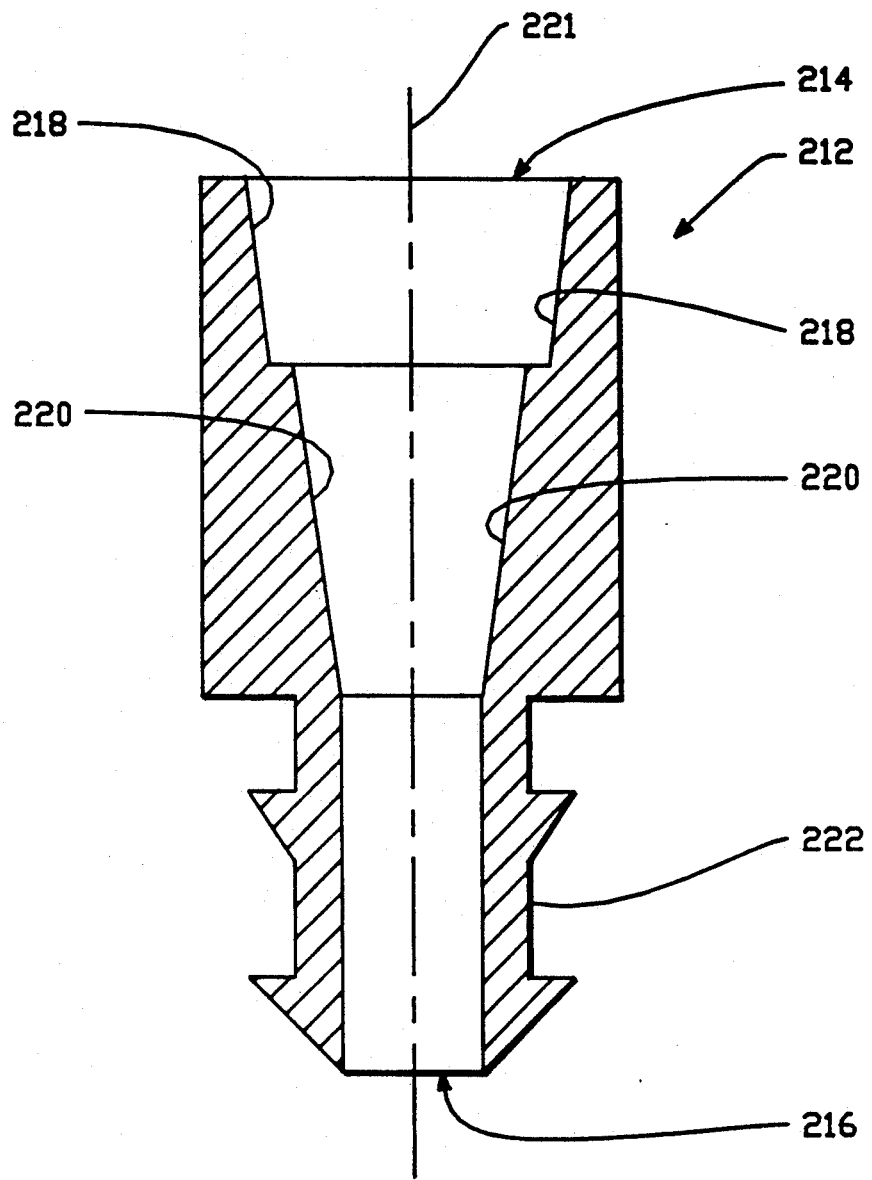
FIG. 13 is a cross-section side elevation view of a ferrule in accordance with the invention.

Referring to the illustrative drawings of FIG. 13, there is shown a cross-sectional view of another ferrule 212 in accordance with the invention. The ferrule 212 defines a conduit extending between an inlet opening 214 and an outlet opening 216. It also defines first and second conical inner wall regions 218, 220, aligned about a central axis 221, that can be used to form respective taper locks with differently sized and contoured connector portions. A barbed stem 222 extends longitudinally along the axis and defines the outlet opening 216. The barbs can be used to secure the ferrule to an enteral tube inlet opening (not shown) so as to adapt such a tube opening to withstand repeated insertions and removals of differently sized connectors without suffering, stretching or wear-and-tear.

Thus, the ferrules 70, 126 in accordance with the present embodiments of the invention advantageously can be used to ensure that connectors such as the first and second connectors 58, 60 can be inserted and removed from an end portion of a feeding tube, without the exertion of undue force and without resulting in unwanted stretching of the end portion. Furthermore, the inner wall regions of the ferrules 70, 126 can be sized and contoured to precisely conform to the shape of a number of different connector portions. While the branched ferrules of FIGS. 11 and 12 include gripping mechanisms in the form of threads 186, taper locks and conical barbs 210, it will be appreciated that alternative gripping mechanisms 7 can be employed. For example, gripping mechanisms like those disclosed in FIGS. 14–20A or other types of gripping mechanisms or other combinations of the illustrated gripping mechanisms could be used without departing from the invention. Furthermore, as shown in FIGS. 11 and 12, multiple types of gripping mechanisms can be employed at each inlet port of a multiple port branched ferrule.

Furthermore, as shown in FIG. 13 and as will be appreciated from the drawings of FIGS. 14–20A, a ferrule can be produced which employs more than one type of gripping mechanism. As explained above in relation to FIGS. 14–20A, while the ferrule 212 includes first and second inner wall regions 218, 220 that can form taper locks and a barbed stem 222, other types and combinations of gripping mechanisms such as steps, threads, offset locks and ball and sockets can be employed without departing from the invention. Also, while only up to three inner wall segments are shown in FIGS. 14–19, additional inner wall segments or exterior wall segments can be employed which include still further gripping mechanisms. Thus, even more than three gripping mechanisms may be used per ferrule. Moreover, while only four inlet branches are shown for each of the two ferrules of FIGS. 11 and 12, it will be understood that additional inlet branches could be added without departing from the invention.

The foregoing description is not intended to limit the invention which is defined in the appended claims in which:

What is claimed is:

1. A feeding device comprising:
   an elongated tube formed from a flexible material;
   an inlet end portion formed from the flexible material and integrally connected to the elongated tube and defining first, second and third inlet port openings;
   a ferrule disposed within said inlet end portion, said ferrule including,
   a first inner wall defining a first main conduit,
   a second inner wall defining a second main conduit,
   a first inlet defining a first inlet conduit and providing fluid communication between the first inlet port opening and said first main conduit,
   a second inlet defining a second inlet conduit and providing fluid communication between the second inlet port opening and said first main conduit,
   a third inlet defining a third inlet conduit that provides fluid communication between said third inlet port opening and said second main conduit.

2. The feeding device of claim 1 wherein:
   said inlet end portion defines a fourth inlet port opening; and wherein said ferrule further includes:
   a fourth inlet defining a fourth inlet conduit that provides fluid communication between said fourth inlet opening and said second main conduit.

3. The feeding device of claim 1;
   wherein the first main conduit is aligned along a first main axis and the first inlet conduit is aligned along a first inlet axis offset from the first main axis; and wherein the second main conduit is aligned along a second main axis and the third inlet conduit is aligned along a second inlet axis offset from the second main axis.

4. The feeding device of claim 1 wherein at least one of said first, second and third inlet ports includes gripping means for making mechanical connection with an external connector.

5. The feeding device of claim 4 wherein said gripping means includes:
   at least one taper lock surface for forming a taper lock with a first external connector having first dimensions.

6. The feeding device of claim 5 wherein said gripping means further includes:
   second taper lock surface for forming a taper lock with a second external connector having second dimensions.

7. The feeding device of claims 4 wherein said gripping means includes a threaded region about a portion of at least one of said first, second and third inlet conduits.

8. The ferrule of claim 4 wherein said gripping means includes a barbed gripping means for gripping an inlet port of a feeding device.

9. A feeding device comprising:
   an elongated tube formed from a flexible material;
   an inlet end portion formed from the flexible material and integrally connected to the elongated tube and defining first, second, third and fourth inlet portion openings;
   a ferrule disposed within said inlet end portion, said ferrule including,
   a first inner wall defining a first main conduit,
   a second inner wall defining a second main conduit,
   a first inlet defining a first inlet conduit that provides fluid communication between the first inlet port opening and said first main conduit,
   a second inlet defining a second inlet conduit that provides fluid communication between the second inlet port opening and said first main conduit;
   a third inlet defining a third inlet conduit that provides fluid communication between the third inlet portion opening and said second main conduit, and
   a fourth inlet defining a fourth inlet conduit that provides fluid communication between said fourth inlet opening and said second main conduit.

10. A feeding device comprising:
    an elongated tube formed from a flexible material;
    an inlet end portion formed from the flexible material and integrally connected to the elongated tube and defining first and second inlet port openings;
    a ferrule disposed within said inlet end portion, said ferrule including,
    a first inner wall defining a first main conduit,
    a second inner wall defining a second main conduit,
    a first inlet defining a first inlet conduit that provides a fluid communication between the first inlet port opening and said first main conduit, and
    a second inlet defining a second inlet conduit providing fluid communication between the second inlet portion opening said second main conduit.

11. The feeding device of claim 10 wherein said first inlet is offset from said first main conduit.

12. The feeding device of claim 10 wherein said first inlet includes gripping means for making mechanical connection with an external connector.

13. The feeding device of claim 10 wherein, the first main conduit is aligned along a first main axis and the first inlet conduit is aligned along a first inlet conduit offset from the first main conduit; and the second main conduit is aligned along a second main axis and the second inlet conduit is aligned along a second inlet conduit offset from the second main conduit.

14. A feeding device comprising:

an elongated tube formed from a flexible material;

an inlet end portion formed from the flexible material; and integrally connected the elongated tube and defining a plurality of respective inlet portion openings;

a ferrule disposed within said inlet end portion, said ferrule including, a first inner wall defining a first main conduit, a second inner wall defining a second main conduit.

a plurality of respective first inlets, each corresponding to a respective inlet port opening, and each for providing fluid communication between a respective inlet port opening and the first main conduit, and a plurality of respective second inlets, each corresponding to a respective inlet port opening, and each for providing fluid communication between a respective inlet port opening and the second main conduit.

* * * * *